(12) United States Patent
Schmelz et al.

(10) Patent No.: US 8,574,317 B2
(45) Date of Patent: Nov. 5, 2013

(54) AQUEOUS COLOURING COMPOSITION

(75) Inventors: Sandra Schmelz, Marktheidenfeld (DE); Alexandra Meuser, Egelsbach (DE)

(73) Assignee: KAO Germany GmbH, Darmstadt (DE)

( * ) Notice: Subject to any disclaimer, the term of this patent is extended or adjusted under 35 U.S.C. 154(b) by 0 days.

(21) Appl. No.: 13/819,480

(22) PCT Filed: Aug. 17, 2011

(86) PCT No.: PCT/EP2011/064126
§ 371 (c)(1),
(2), (4) Date: Feb. 27, 2013

(87) PCT Pub. No.: WO2012/028456
PCT Pub. Date: Mar. 8, 2012

(65) Prior Publication Data
US 2013/0167863 A1   Jul. 4, 2013

(30) Foreign Application Priority Data
Sep. 3, 2010  (EP) .................................... 10009162

(51) Int. Cl.
*A61Q 5/10*  (2006.01)

(52) U.S. Cl.
USPC ................ 8/405; 8/406; 8/408; 8/435; 8/552; 8/557; 8/558

(58) Field of Classification Search
USPC .............. 8/405, 406, 408, 435, 552, 557, 558
See application file for complete search history.

(56) References Cited

U.S. PATENT DOCUMENTS

| 4,685,931 | A | 8/1987 | Schiefersteub et al. |
| 4,985,239 | A | 1/1991 | Yahagi et al. |
| 6,106,577 | A | 8/2000 | Audousset et al. |
| 6,126,921 | A | 10/2000 | Emmerling et al. |
| 2002/0194683 | A1* | 12/2002 | Casperson et al. ................ 8/405 |
| 2006/0064823 | A1 | 3/2006 | Marsh et al. |
| 2009/0119852 | A1 | 5/2009 | Marsh |
| 2011/0117042 | A1 | 5/2011 | Viala et al. |

FOREIGN PATENT DOCUMENTS

| DE | 4108259 A1 | 12/1991 |
| EP | 0 808 624 A2 | 11/1997 |
| EP | 2 145 616 A1 | 1/2010 |

OTHER PUBLICATIONS

International Search Report Dated Feb. 17, 2012, Mailed Feb. 27, 2012.

* cited by examiner

*Primary Examiner* — Eisa Elhilo
(74) *Attorney, Agent, or Firm* — Norris McLaughlin & Marcus P.A.

(57) ABSTRACT

The present invention is related to an aqueous oxidative colouring composition for keratin fibres, especially human hair. The present invention is on an aqueous composition for colouring keratin fibres especially human hair comprising at least one hair dye, at least one oxidizing agent and at least one dispersed particles of a water insoluble polymer. Furthermore, the present invention is on a two part aqueous dyeing composition, wherein the two parts are mixed prior to application onto keratin fibres especially human hair wherein the aqueous first part comprises at least one hair dye and the aqueous second part comprises at least one oxidizing agent and at least one dispersed particles of a water insoluble polymer.

10 Claims, No Drawings

United States Patent US 8,574,317 B2

AQUEOUS COLOURING COMPOSITION

This application is a 371 application of PCT/EP2011/064126 filed Aug. 17, 2011,which claims foreign priority benefit under 35 U.S.C.§119 if European Application No. 10009162.8 filed Sep. 3, 2010.

The present invention is related to an aqueous oxidative colouring composition for keratin fibres, especially human hair.

Hair colouring has been widely practiced for ages. The colorations are divided into two main groups, the first being permanent colouration based on mainly oxidative hair dyes which penetrate into hair and polymerize, and the second is based on direct dyes which is, without excluding any penetration, mainly adsorbed onto hair and widely based on cationic and neutral dyes. In the latter, recently compositions based on anionic direct dyes have also been made available by the applicant which deliver brilliant, shiny and long lasting colours.

In hair colouration, one of the purposes is certainly change the hair colour and/or cover any inhomogeneous hair colours in particular grey hair. Another purpose is to refresh shine, brilliance and vibrancy of hair colour. Especially in hair shine wide variability has been observed and there is, therefore, need for further improvements.

In oxidative hair colouring, achieving homogeneous colours is one of the most important targets. Inhomogenity is usually a result of different level of hair damage in length of hair. In other words, towards roots hair is healthy or healthier and towards tips hair is damaged. Due to the differences in damage level, dye penetration varies as well. Therefore, there is a need for new technologies to overcome such problems.

Hair colouration, especially oxidative hair colouring may damage the hair which may further cause that hair becomes difficult to comb through, is not smooth, difficult to manage and has too many fly-aways. It is therefore, desirable to have hair colouring compositions which does not have at least one of these disadvantages and optimally none of these disadvantages.

The present invention starts with the above mentioned problems especially of unsatisfactory hair condition after oxidative hair colouring and aims at providing an oxidative hair colouring composition which does not show at least one of the above mentioned disadvantages.

The inventor of the present invention have surprisingly found out that an aqueous composition comprising at least one hair dye, at least one oxidizing agent and at least one dispersed particles of a water insoluble polymer colours hair excellently homogeneously and improves hair conditions in terms of shine, combability and manageability and especially hair coloured with such composition feels soft and smooth and has less fly-aways.

Accordingly, the first object of the present invention is an aqueous composition for colouring keratin fibres especially human hair comprising at least one hair dye, at least one oxidizing agent and at least one dispersed particles of a water insoluble polymer.

It has further been found out that the aqueous colouring composition of the present invention is a two part dye composition for keratin fibres especially human hair wherein the first part comprises at least one hair dye and the second part comprises at least one oxidizing agent and at least one dispersed particles of a water insoluble polymer colours keratin fibres and especially human hair excellently homogeneously and conditions hair in terms of shine, combability and manageability and especially hair coloured with such composition feels soft and smooth and has less fly-aways.

Accordingly, the second object of the present invention is a two part aqueous dyeing composition, wherein the two parts are mixed prior to application onto keratin fibres especially human hair wherein the aqueous first part comprises at least one hair dye and the aqueous second part comprises at least one oxidizing agent and at least one dispersed particles of a water insoluble polymer.

Further object of the present invention is the use of the dispersed particles of a water insoluble polymer in an aqueous oxidative colouring composition comprising at least one hair dye and at least one oxidizing agent for conditioning human hair especially improving shine, combability, softness, smoothness and manageability.

Further object of the present invention is a kit for colouring hair comprising at least two composition wherein the first composition is an aqueous composition and comprises at least one hair dye and the second composition is an aqueous composition and comprises at least one oxidizing agent and at least one dispersed particles of a water insoluble polymer.

Within the meaning of the present invention it is meant with the term "water insoluble polymer" that the polymer is practically insoluble in water at any temperature hair colouring is carried out, i.e. up to 50° C.

Suitable particles of water insoluble polymer comprises at least one monomer of styrene, acrylic or methacrylic acids, preferably is of styrene-acrylic acid polymer. Polymers suited are of anionic or non-ionic ones, preferred ones are non-ionic polymers. Most preferred particles of water insoluble polymer dispersed in water is of styrene-acrylates colpolymer available from Interpolymer under the trade name Syntran 5905.

Concentration of dispersed particles of a water insoluble polymer is in the range of 0.001 to 5%, preferably 0.01 to 3% and more preferably 0.02 to 2% and most preferably 0.05 to 1% by weight calculated to total composition.

It should be noted that within the meaning of the present invention all concentrations described are calculated to total composition prior to any mixing.

Composition especially the aqueous first part composition comprises at least one hair dye which may be selected from oxidative and direct dyes. In a preferred embodiment of the present invention, the aqueous composition or the first part aqueous composition comprises at least one direct dye or at least one oxidative dye precursor and optionally at least one coupling agent. In a further preferred embodiment, the aqueous composition or the first part aqueous composition comprises at least one oxidative dye precursor, at least one direct dye and optionally at least one coupling agent.

As a rule, it is possible to incorporate any developing substances known per se. Special mention is made of p-phenylenediamine, p-aminophenol and substituted p-phenylenediamines such as 2,5-diamino-toluene, 2-n-propyl or 2-ethyl-p-phenylenediamine, 2,6-di-methyl-p-phenylene-diamine, 2-(2,5-diaminophenyl) ethanol, 1-amino-4-bis-(2'-hydroxyethyl)amino-benzene, 2-(2-hydroxyethyl amino)-5-amino-toluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethylamino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene, pyrazole and the derivatives thereof such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 3,5-diamino-1,2,4-triazole, 4-aminophenol and the derivatives thereof such as 4-amino-3-methylphenol, 2-chloro-4-aminophenol, 2,6-dichloro-4-aminophenol, 2,4-diamino-phenol, 2,6-dibromo-4-aminophenol, tetramino pyrimidines, triaminohydroxy pyrimidines, diaminomono- and -dihydroxy pyrimidines, aminotriazines, 5-amino salicylic acid and/or 1,2,4-triamino benzene or the water-soluble salts thereof.

Further suitable ones aminopyridines are 2,5-diaminopyridine, 2,3-diaminopyridine, 2,6-diaminopyridine, 3-amino-2-methyl amino-6-methoxypyridine, 2-dimethyl-5-aminopyridine, 2-dimethyl aminoethyl-3-hydroxypyridine, 2-amino-4,6-dimethyl pyridine, 2-amino-3-hydroxypyridine, 3-amino-2(β-hydroxyethyl amino)-6-methoxy-pyridine, 2,6-dimethyl amino-5-aminopyridine, 2-di(hydroxyethyl)amino-5-aminopyridine, 2-hydroxyethyl amino-5-aminopyridine, 4-hydroxy-2,5,6-triaminopyrimidine and/or the water-soluble salts thereof.

Within the meaning of the present invention above mentioned developers can as well be present as a mixture of each other.

The total concentration of the dye precursors (developing substances) customarily ranges between 0.001 to 5%, preferably 0.01 to 4% and more preferably 0.05 to 3%, and most preferably 0.1 to 2% by weight, calculated to the total composition prior to mixing with oxidizing agent.

In a further embodiment of the present invention the aqueous composition or first part aqueous composition comprises in addition to at least one oxidative dye precursor at least one coupling substance. As a rule any coupling substance customarily used in oxidative hair colouration area is suitable within the meaning of the present invention. Non-limiting coupling substances, are 5-amino-2-methylphenol, 2-methyl-5-hydroxyethylaminophenol, 2,4,-diamnophenoxyehanol, 2-amino-4-hydroxyethylaminoanisol, 2-methyl-5-amino-6-chlorphenol, 1,3-bis(2,4-diaminophenoxy)propane, 2-bis(2-hydroxyethyl)aminotoluene, 2-amino-5-methylphenol, resorcinol, 2-methyl-resorcinol, 4-chlororesorcinol, 2-amino-4-chlorophenol, 5-amino-4-methoxy-2-methylphenol, 2-aminophenol, 3-amino-phenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 1,3-diamino-benzene, 1-amino-3-(2'-hy-droxyethylamino)benzene, 1-amino-3-[bis(2'-hydroxy-ethyl)amino]benzene, α-naphthol, 4,6-dichlororesorcinol, 1,3-diamino-toluene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2-methoxyphenol and/or 1-methoxy-2-amino-4-(2'-hydroxyethyl amino)benzene or the water-soluble salts thereof. One or more of the above mentioned coupler can also be used in a mixture.

In the hair dyeing compositions according to the invention, the coupling substance(s) as reaction partners of the developing substance(s) are present in approximately the same molecular proportions as the developing substances, i.e. in amounts from 0.001 to 5%, preferably 0.01 to 4% and more preferably 0.05 to 3%, and most preferably 0.1 to 2% by weight, calculated to the total composition prior to mixing with oxidizing agent.

Further, indole and indoline derivatives can as well be contained in the colouring composition of the present invention. Examples to those are: 6-aminoindol, 6-hydroxyindole, 1-ethyl-6-hydroxyindole, 1-methyl-4-hydroxyindol, 1-methyl-6-hydroxyindole, 2-methyl-6-hydroxyindole, 5-hydroxyindol, 4-hydroxyindol, 5,6-dihydroxyindole, 6-aminoindoline, 6-hydroxyindoline, 1-ethyl-6-hydroxyindoline, 1-methyl-4-hydroxyindoline, 1-methyl-6-hydroxyindoline, 2-methyl-6-hydroxyindoline, 5-hydroxyindoline, 4-hydroxyindoline, 5,6-dihydroxyindoline and their respective salts.

Suitable direct dyes are cationic, anionic, neutral dyes and mixtures thereof as available commercially from various suppliers.

One of the suitable direct dyes is cationic dyes. Non-limiting examples are Basic Blue 6, Basic Blue 7, Basic Blue 9, Basic Blue 26, Basic Blue 41, Basic Blue 99, Basic Brown 4, Basic Brown 16, Basic Brown 17, Basic Orange 31, Natural Brown 7, Basic Green 1, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87, and their salts such as chloride, methosulfate, bromide etc. and mixtures thereof.

Further suitable direct dyes are anionic dyes. Suitable non-limiting examples are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium, and their mixtures.

Further suitable dyes for colouring hair within the meaning of the present invention are those of neutral nitro dyes. Suitable non-limiting examples are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid, and their mixtures.

Plant dyestuffs may also be used as hair colorant within the meaning of the present invention for example henna (red or black), alkanna root, laccaic acid, indigo, logwood powder, madder root and rhubarb powder, etc.

Among the direct dyes cationic and nitro dyes are preferred ones. Most preferred ones are cationic direct dyes.

Concentration of direct dyes in the compositions of the present invention is within the range of 0.001 to 10%, preferably 0.01 to 7.5% and more preferably 0.05 to 5%, and most preferably 0.1 to 3% by weight, calculated to total composition prior to mixing with oxidizing agent.

Aqueous composition and the second part of the two part composition comprise at least one oxidizing agent. The oxidizing agents suitable are hydrogen peroxide, urea peroxide, melamin peroxide or perborate salts. The most preferred is hydrogen peroxide, which is used as a lotion containing 2 to 12% by weight, calculated to composition prior to mixing with the aqueous first part.

The aqueous two parts of the two part colouring composition are mixed immediately prior to application onto hair. The mixing ratio of the first and second aqueous compositions is in the range of 4:1 to 1:4, by weight, preferably 2:1 to 1:3 by weight of the first to second aqueous compositions.

pH of the aqueous composition and the composition resulting from mixing of the two part composition is in the range of 6 to 12, preferably 6.5 to 11 and more preferably 6.8 to 10 (the values are included). pH of the first composition is alkaline and in the range of 8 to 12 and the pH of the second composition is acidic and in the range of 1 to 6, preferably 2 to 5 and more preferably 2 to 4, and most preferably 2.5 to 3.5.

In a further preferred embodiment of the present invention, the aqueous first part composition comprises at least one alkalizing agent, preferably selected from ammonia, alklanolamines especially monoethanolamine and carbonates or bicarbonates and their mixtures. The second part aqueous composition comprises at least one acidic compound which may be organic or inorganic or their mixtures, preferably phosphoric acid.

Aqueous colouring composition and any part of the two part composition according to the present invention can be in the form of emulsion, solution, dispersion, thickened liquid, gel, foam and powder. Emulsion form is the preferred form for the aqueous colouring composition and for the first part aqueous composition. The preferred forms of the second part composition are dispersion and emulsion.

With the term thickened liquid, it is meant that the composition comprises additionally a thickening agent.

With the term gel it is meant that the composition comprises additionally a gelling agent and the gelling agent is a polymer forming a shear thinning gel.

The thickening agents include any polymer either natural or synthetic thickening agents for aqueous composition. Examples are cellulose and its derivatives such as hydroxyethylcellulose, guar and its derivatives such as hydroxypropyl guar. In the selection of the thickening agent compatibility with any other components of the formulation should carefully be examined.

The gelling agents include polymers either synthetic or natural forming shear thinning compositions. Examples to the natural polymers are xanthan gum and its derivatives. Synthetic shear thinning polymers may be those of acrylate polymers commercially available for example under trade name Carbopol. In the selection of the gelling agent compatibility with any other components of the formulation should carefully be examined.

It should be noted that gelling and thickening agents can also be used in mixture. Concentration of the thickening and/or gelling agents should be in the range of 0.05 to 5%, preferably 0.1 to 2.5% by weight calculated to total composition prior to mixing with oxidizing agent.

Composition and any part of the two part composition of the present invention further comprise at least one surfactant selected from non-ionic, cationic, anionic and amphoteric ones and their mixtures.

Suitable non-ionic surfactants are alkyl polyglucosides of the general formula

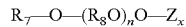

$$R_7-O-(R_8O)_n O-Z_x$$

wherein $R_7$ is an alkyl group with 8 to 18 carbon atoms, $R_8$ is an ethylene or propylene group, Z is a saccharide group with 5 to 6 carbon atoms, n is a number from 0 to 10 and x is a number between 1 and 5. Examples are decyl polyglucoside, cocoyl polyglucoside both are commercially available.

Further nonionic surfactant components are, for example, long-chain fatty acid mono- and dialkanolamides, such as coco fatty acid monoethanolamide and myristic fatty acid monoethanolamide.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®".

Further nonionic surfactants as emulsifiers useful in the compositions according to invention are $C_{10}$-$C_{22}$-fatty alcohol ethoxylates. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16":

The average degree of ethoxylation thereby ranges between about 2.5 and about 50, preferably about 10 and about 30.

Among the non-ionic surfactants mentioned above fatty alcohol ethoxylates are the most preferred ones. Above mentioned non-ionic surfactants can also be used as mixture of one category such as several ethoxylated fatty alcohols or several categories such as mixture of alkyl polyglucoside and ethoxylated fatty alcohol.

As further surfactant suitable for the compositions according to the present invention are amphoteric or zwitterionic surfactants. Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate.

Further surfactants suitable within the meaning of the present invention are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof.

Additional anionic surfactants useful are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula

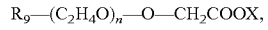

$$R_9-(C_2H_4O)_n-O-CH_2COOX,$$

wherein $R_9$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted.

Further suitable anionic surfactants are also $C_8$-$C_{22}$-acyl aminocarboxylic acids or the water-soluble salts thereof, such as N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in mixture with the above-named anionic surfactants.

Further according to an embodiment, aqueous compositions comprise at least one cationic surfactant according to general formula

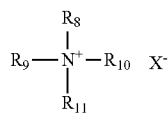

where $R_8$ is a saturated or unsaturated, branched or non-branched alkyl chain with 8-24 C atoms $R_9$ is a hydrogen, saturated or unsaturated, branched or non-branched alkyl chain with 1-24 C atoms and $R_{10}$ and $R_{11}$ are independent from each other H or lower alkyl chain with 1 to 4 carbon atoms which may be substituted with one or two hydroxyl group, and X is chloride, bromide or methosulfate.

Concentration of cationic surfactant is in the range from 0.05% to 5%, preferably 0.1% to 2.5% by weight, calculated to total composition prior to mixing with oxidizing agent.

Non-limiting suitable long-chain quaternary ammonium compounds which are in particular cetyl trimethyl ammonium chloride, dimethyl dicetyl ammonium chloride, trimethyl cetyl ammonium bromide, stearyl trimethyl ammonium chloride, dimethyl stearyl hydroxyethyl ammonium chloride, lauryl trimethyl ammonium chloride etc.

Total surfactant concentration varies between 0.1 and 15%, preferably 0.5 and 10%, and more preferably 1 to 7.5% by weight calculated to total composition prior to mixing with oxidizing agent.

Any aqueous composition of the present invention can be in the form of emulsion especially oil in water (O/W) emulsion. Emulsions according to the present invention preferably comprise at least one fatty alcohol with linear of branched alkyl chain. Suitable ones are fatty alcohols having 12 to 22 C atoms in its alkyl chain. Examples are myristyl alcohol, cetyl alcohol, stearyl alcohol, behenyl alcohol and their mixtures. Preferred are cetyl, stearyl and behenyl alcohol and their mixtures i.e. cetearyl alcohol. Fatty alcohols may be included into the compositions of the present invention at a concentration of 0.1 to 20%, preferably 0.5 to 15% and more preferably 1 to 10% by weight calculated to total composition prior to mixing with oxidizing agent.

Emulsions should also comprise at least one emulsifier. Suitable emulsifiers are those surfactants mentioned above. Preferred emulsifiers are non-ionic, cationic and anionic surfactant mentioned above. Among the non-ionic surfactant fatty alcohol ethoxylates are the most proffered ones. Among cationic surfactants any cationic surfactant with a single alkyl chain is suitable. Sulfate types of anionic surfactants are the preferred anionic surfactants. The above mentioned concentrations are also suitable for the emulsifiers mentioned here.

Aqueous composition and the first part aqueous composition of present invention can comprise additionally fatty acids with 0 to 3 ethylenic bonds and with fatty acyl chain length of 12 to 22 C atom. Concentration of the fatty acids can be in the range of 0.1 to 10%, preferably 0.1 to 7.5% and most preferably 0.2 to 5% by weight calculated to the total composition prior to mixing with oxidizing agent. Fatty acid examples, without limiting the choice, suitable for colouring compositions are myristic acid, palmitic acid, behenic acid, steraic acid, oleic acid, linoleic acid. The most preferred fatty acid is oleic acid.

Any aqueous composition of the present invention may comprise additionally hair conditioning compounds such as oils, cationic polymers, non-ionic substances. Oils as conditioners according to the present invention are selected from silicone oils either volatile or non-volatile, natural and synthetic oils. Among silicone oils those can be added to the compositions include either volatile or non-volatile dimethicone, dimethiconol, polydimethylsiloxane, DC fluid ranges from Dow Corning, cyclosiloxanes such as DC 245. Synthetic oils include mineral oil such as paraffin oil and petrolatum.

Arylated silicones have been found to be especially suitable for the compositions of the present invention at a concentration range of 0.01 to 5%, preferably 0.05 to 4% more preferably 0.1 to 3% and most preferably 0.1 to 2.5% by weight calculated to total composition prior to mixing with oxidizing agent. Non-limiting suitable examples are phenyl methicone, phenyl trimethicone, diphenyl dimethicone, diphenylsiloxy phenyl trimethicone, tetramethyl tetraphenyl trisiloxane, triphenyl trimethicone, tetramethly tetraphenyl trisiloxane and trimethyl pentaphenyl trisiloxane.

Particularly preferred arylated silicone is trimethyl pentaphenyl trisiloxane available from Dow Corning under the trade name DC PH-1555 HRI.

It should be noted that compositions of the present invention can also comprise more than one arylated silicone.

Natural oils suitable are such as olive oil, almond oil, avocado oil, ricinus oil, coconut oil, palm oil, sesame oil, peanut oil, whale oil, sunflower oil, peach kernel oil, wheat germ oil, macadamia nut oil, night primrose oil, jojoba oil, castor oil, or soya oil, lanolin and the derivatives thereof.

Lipophilic oily compounds such as fatty acid esters are also suitable for the composition of the present invention. Examples are such as isopropyl myristate, palmitate, stearate and isostearate, oleyl oleate, isocetyl stearate, hexyl laurate, dibutyl adipate, dioctyl adipate, myristyl myristate, oleyl erucate, cetyl palmitate, etc. Non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula

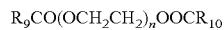

where $R_9$ and $R_{10}$ are independent from each other saturated, unsaturated or branched or non-branched alkyl chain with 7 to 21 C atoms and n is typically 2-100.

Any aqueous composition of the present invention can comprises cationic polymers as conditioning agents. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, it has especially been found suitable those cationic polymers known with their CTFA category name Polyquaternium. Typical examples of those Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, Polyquaternium 46, Polyquaternium 67 and Polyquaternium 87.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-82, Quaternium-83 and Quaternium-84.

In this context, reference is also made to the cationic polymers disclosed in DE 25 21 960, 28 11 010, 30 44 738 and 32 17 059, as well as to the products described in EP-A 337 354 on pages 3 to 7. It is also possible to use mixtures of various cationic polymers.

Further cationic polymers are so called aminated silicones such as amodimethicone. The cationic polymers also include the quaternized products of graft polymers from organopolysiloxanes and polyethyl oxazolines described in EP-A 524 612 and EP-A 640 643.

Concentration range for any of the additional conditioners mentioned above is in the range of 0.01 to 10% by weight, preferably 0.05-7.5% by weight, more preferably 0.1-5% by weight calculated to the total composition.

The compositions according to the present invention can also comprise further agents, such as protein hydrolyzates and polypeptides, e.g. keratin hydrolyzates, collagen hydrolyzates of the type "Nutrilan" or elastin hydrolyzates, as well as, in particular vegetable, optionally cationized protein hydrolyzates, for example "Gluadin".

Additional natural plant extracts can as well form part of the compositions of the present invention. Those are incorporated usually in an amount of about 0.01% to about 10%, preferably 0.05% to 7.5%, in particular 0.1% to 5% by weight, calculated as dry residue thereof to the total composition. Suitable aqueous (e.g. steam-distilled) alcoholic or hydro-alcoholic plant extracts known per se are in particular extracts from leaves, fruits, blossoms, roots, rinds or stems of aloe, pineapple, artichoke, arnica, avocado, valerian, bamboo, green tea, blue lotus flower, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, cocoanut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc. Suitable trade products are, for example, the various "Extrapone" products and "Herbasol®". Extracts and the preparation thereof are also described in "Hagers Handbuch der pharmazeutischen Praxis", $4^{th}$ Ed.

The compositions can contain one or more organic solvents such as ethanol. propanol, isopropanol, benzyl alcohol, benzyloxyethanol, alkylene carbonates such as ethylene carbonate and propylene carbonate, phenoxyethanol, butanol, isobutanol, cyclohexane, cyclohexanol, hexyleneglycol, ethylenecarbonate, ethyleneglycol monoethylether, ethylene glycol monobutyl ether, ethylene glycol monophenyl ether, 1-phenylethylalcohol, 2-phenylethylalcohol, o-methoxyphenol. Concentration of organic solvent can be in the range of 1 to 40%, preferably 1 to 25% by weight, calculated to total composition prior to mixing with oxidizing agent.

Compositions of the present invention can comprise UV filters for protection of hair from environmental influences such as loss of elasticity, loss of hair colour (bleaching effect of sun light). The UV-absorbing substance is preferably selected from the following compounds: 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2.4-dihydroxybenzophenone, 2.2'.4.4'-tetrahydroxy-benzophenone, 2-hydroxy-4-methoxybenzophenone and its 5-sulfonic acid or the sodium salt thereof, 2,2'-dihydroxy-4,4'-dimethoxybenzophenone, 2-hydroxy-5-chlorobenzophenone, 2,2'-dihydroxy-4-methoxybenzophenone, 2.2'-dihydroxy-4.4'-dimethoxy-5.5'-disulfobenzo-phenone or the sodium salt thereof, 2-hydroxy-4-octyloxybenzophenone, 2-hydroxy-4-methoxy-4'-methylbenzophenone, 3-benzyl-idenecampher, 3-(4'-sulfo)-benzyl-idenebornane-2-one and the salts thereof and/or 3-(4'-methyl benzylidene)-DL-campher, polysilicone-15. The preferred amount of the UV-absorber ranges from about 0.01% to 2.5%, more preferably from 0.05% to 1% by weight, calculated to the total composition.

The compositions of the present invention can comprise one or more hair-restructuring agents. The hair restructuring agents preferred are especially the ones disclosed in the German patent DE 197 51 550 C2. Namely they are ceramide type of compounds, fatty acids and phytosterol or their mixtures.

Preferred ceramide compound is cetyl-PG-hydroxyethylpalmitamide.

Preferred fatty acids are those with 10 to 24 carbon atoms and especially with 16 to 24 carbon atoms.

Sterols, especially the phytosterols, are as well preferred hair restructuring agents as disclosed in the above mentioned german patent. Especially preferred ones are of plant origin for example ergosterol, sitosterol, stigmasterol, fucosterol, brassicasterol, fungisterol, campesterol, zymosterol, ascosterol, cerevisterol, episterol, faecosterol, spinasterol. Among those phytosterols, the ones found in "Avocadin" which is the unsaponified fraction of the avocado oil is more preferred.

The concentration of ceramide in the compositions of the present invention can be in the range of 0.01 to 2% and especially 0.01 to 1% by weight calculated to the total composition prior to mixing with oxidizing agent. The fatty acids may be contained at a level of 0.01 to 2.5% and especially 0.01 to 1% by weight calculated to the total composition prior to mixing with oxidizing agent. Phytosterol concentration of the conditioners is less than 1% and preferably in the range of 0.01 to 0.5% by weight calculated to the total composition prior to mixing with oxidizing agent. It should be noted without limiting the use of those ingredients the effect of those hair restructuring ingredients is especially elevated when used in combination with penetration enhancers.

Any aqueous compositions of the present invention may comprise further at least one compound according to the formula

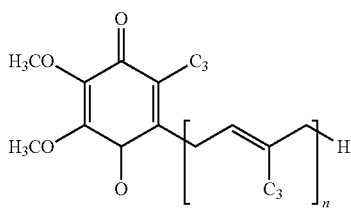

where n is a number from 1 to 10.

The compounds of the above formula are known as Ubiquinone, and also are known as Coenzyme. It should be noted that the compositions of the present invention can certainly comprise more than one ubiqinone. Preferred ubiqinones are the ones where n is a number between 6 and 10 and especially preferred is Ubiqinone 50 where n is 10, also known as Coenzyme Q10. Concentration ubiqinone of the above formula in the compositions is from 0.0001 to 1%, preferably from 0.0002 to 0.75%, more preferably from 0.0002 to 0.5% and most preferably from 0.0005 to 0.5% by weight, calculated to total composition prior to mixing with oxidizing agent.

Any aqueous composition of the present invention may further comprise particulate matter such as synthetic mica. Use of synthetic mica coated with metal oxide or oxides mainly in decorative cosmetics is disclosed in an international patent application of Sun Chemical Corporation published with a number WO 2005/065632 A1. In the document synthetic mica and coated synthetic mica with at least one metal oxide or oxides is disclosed in detail, the content of the document is included herewith by reference.

Suitable metal oxide or oxides for coating synthetic mica are titanium dioxide, chromium oxide, ferric oxide or mixtures thereof. In the present invention the preferred is synthetic mica coated with titanium dioxide. Such materials are commercially available from Sun Chemical Corporation and are known with their INCl names Synthetic Fluorphologopite.

The particle size distribution of synthetic mica coated with a metal oxide or oxides is in the range of 1 to 750 μm, preferably 1 to 250 μm, more preferably 1 to 100 μm and most preferably 20 to 95 μm. The particle sizes referred are relating to the volume particle size distribution meaning that particles found in the coated synthetic mica having volume particle size in the given ranges.

Concentration of synthetic mica coated with at least metal oxide or oxides is from 0.001 to 10%, preferably 0.05 to 7.5%, more preferably 0.1 to 5% and most preferably 0.25 to 2.5% by weight calculated to total composition prior to mixing with oxidizing agent.

Any of the aqueous compositions may comprise at least one dipeptide. With the term dipeptide, compounds with two amino acid moieties are meant. In principal any dipeptide available either natural or synthetic are suitable for the purposes of the present invention. The synthetic ones are preferred. In one of the preferred embodiment of the present invention the amino acid moeities are selected from arginine, tyrosine, valine, tryptophan, alanine, cysteine, glycine, lysine, proline, hydroxyproline and histidine. The dipetides according to the present invention may certainly be of two different amino acids but at the same time two of the same amino acids. In a further preferred embodiment of the present invention, the two amino acid moieties are of different amino acids when one of the amino acid moieties is glycine and more preferably are of two different amino acids.

Non-limiting examples to the suitable dipeptides are the ones commercially available and known with their INCl name as Dipeptide-1, Dipeptide-2, Dipeptide-3, Dipeptide-4, Dipeptide-5, Dipeptide-6, Dipeptide-7, Dipeptide-8, and carnosine. The most preferred is carnosine and is containing β-alanin and L-histidine.

Concentration of at least one dipeptide is in the range of 0.01 to 5%, preferably 0.05 to 3% and more preferably 0.1 to 2.5% and most preferably 0.2 to 1.5% by weight calculated to the total composition prior to mixing with oxidizing agent.

Furthermore, compositions of the present invention can comprise all substances customarily found in such preparations. Examples of such substances are complexing agents, preservatives, fragrances, and antioxidants where appropriate such as sodium sulfit.

A further object of the present invention is process for colouring keratin fibres especially human hair wherein an aqueous composition comprising at least one hair dye, at least one oxidizing agent and at least one dispersed particles of a water insoluble polymer is applied onto keratin fibres especially human hair and left for a period of 1 to 45 min and rinsed off and optionally dried.

Still further object of the present invention is a process for colouring hair wherein an aqueous composition comprising at least one hair dye is mixed with an aqueous composition comprising at least one oxidizing agent and at least one dispersed particles of a water insoluble polymer is applied onto keratin fibres especially human hair and left for a period of 1 to 45 min and rinsed off and optionally dried.

Following examples are to illustrate the invention but not to limit.

EXAMPLE 1

|  | % by weight |
|---|---|
| First part composition | |
| Cetearyl alcohol | 10.0 |
| Cocamide MEA | 4.0 |
| Sodium lauryl sulphate | 1.5 |
| Propylene glycol | 2.0 |
| Cetyltrimonium chloride | 0.5 |
| 2,5,6-Triamino-4-hydroxypyrimidine sulphate | 0.01 |
| 2,5-Diaminotoluene sulphate | 0.55 |
| 4-Chlorresorcinol | 0.17 |
| Resorcinol | 0.05 |
| 3-Aminophenol | 0.03 |
| Sodium sulfite | 1.0 |
| Ammonium hydroxide | 8.0 |
| Fragrance, preservative | q.s. |
| Water | to 100 |
| Second part composition | |
| Hydrogen peroxide | 6.0 |
| Disodium phosphate | 0.1 |
| Sodium laureth sulphate | 1.0 |
| Syntran 5905 | 0.2 |
| Water | to 100 |

For comparative purposes the same composition was produced without Syntran 5905, it was replaced with water.

The above composition was tested in a half side test against the comparative composition with 10 consumers having shoulder length hair. The above composition was mixed with a composition comprising 6% hydrogen peroxide at a weight ratio of 1 to 1 and applied onto hair and processed for 30 min at a temperature of 40° C. and rinsed off. Comments from the consumer were the side coloured with the inventive composition is more homogeneously coloured, felt soft and combable and the colour achieved with the inventive composition had significantly more shine and brilliance compared to the side coloured with comparative composition. 9 volunteers preferred the side according to the invention and 1 could not see any difference.

Similar results were observed with the following dyeing compositions.

EXAMPLE 2

|  | % by weight |
| --- | --- |
| Cetearyl alcohol | 10.0 |
| Cocamide MEA | 4.0 |
| Sodium lauryl sulphate | 1.5 |
| Propylene glycol | 2.0 |
| Stearamidopropyldimethylamine | 0.5 |
| Basic red 51 | 0.10 |
| Monoethanolamine | 2.5 |
| Ammonium hydroxide | 5.5 |
| Fragrance, preservative | q.s. |
| Water | to 100 |

The above composition was mixed with aqueous oxidizing composition of Example 1 and applied onto hair. It was found out that hair was homogeneously coloured and felt soft and smooth and easily combable.

EXAMPLE 3

|  | % by weight |
| --- | --- |
| First part composition | |
| Cetearyl alcohol | 10.0 |
| Cocamide MEA | 4.0 |
| Sodium lauryl sulphate | 1.5 |
| Propylene glycol | 2.0 |
| Carnosine | 0.4 |
| Dioleoylethylhydroxyethylmonium methosulfate | 0.75 |
| Phenyl trimethicone | 0.2 |
| 2,5,6-Triamino-4-hydroxypyrimidine sulphate | 0.02 |
| 2,5-Diaminotoluene sulphate | 0.43 |
| HC Yellow 5 | 0.10 |
| 4-amino hydroxytoluene | 0.02 |
| Resorcinol | 0.10 |
| m-aminophenol | 0.07 |
| Sodium sulfite | 1.0 |

-continued

|  | % by weight |
| --- | --- |
| Monoethanolamine | 4.0 |
| Ammonium hydroxide | 4.0 |
| Fragrance, preservative | q.s. |
| Water | to 100 |
| Second part composition | |
| Hydrogen peroxide | 6.0 |
| Disodium phosphate | 0.1 |
| Sodium laureth sulphate | 1.0 |
| Cetearyl alcohol | 1.0 |
| Syntran 5905 | 0.2 |
| Water | to 100 |

Similar results were observed as in Example 1.

The invention claimed is:

1. Aqueous composition for colouring keratin fibres especially human hair, comprising at least one hair dye, at least one oxidizing agent and at least one dispersed particle of a styrene-acrylates copolymer.

2. Composition according to claim 1, wherein the at least one styrene-acrylates copolymer is comprised at a concentration of 0.001 to 5% by weight calculated to total composition.

3. Composition according to claim 1, wherein the at least one hair dye is direct or oxidative dye.

4. Composition according to claim 1, wherein the oxidizing agent is hydrogen peroxide.

5. The composition according to claim 1 further, comprising at least one fatty alcohol.

6. Composition according to claim 1 further, comprising at least one surfactant selected from anionic, nonionic, amphoteric and cationic ones.

7. The composition according to claim 1, wherein the composition further comprises at least one alkalizing agent.

8. The composition according to claim 1, further comprising at least one alkalizing agent.

9. A process for coloring hair with a composition according to claim 1 which composition is a two part hair dye composition which comprises a first aqueous composition comprising at least one hair dye and a second aqueous composition comprising at least one oxidizing agent and at least one dispersed particle of a styrene-acrylates copolymer which two said aqueous compositions are mixed with each other and applied onto hair and after processing for a time of 1 to 45 min, is rinsed off from hair.

10. A kit for colouring hair comprising at least two compositions wherein the first composition is an aqueous composition and comprises at least one hair dye, and the second composition is an aqueous composition and comprises at least one oxidizing agent and at least one particle styrene-acrylates copolymer.

* * * * *